(12) United States Patent
Sander (10) Patent No.: US 12,193,856 B2
(45) Date of Patent: Jan. 14, 2025

(54) DEVICE FOR IMPLEMENTING A LOCKING FUNCTION OF AN ADJUSTMENT AXIS OF AN X-RAY C-ARM SYSTEM

(71) Applicant: Ziehm Imaging GmbH, Nuremberg (DE)

(72) Inventor: Thomas Sander, Nuremberg (DE)

(73) Assignee: Ziehm Imaging GmbH, Nuremberg (DE)

( * ) Notice: Subject to any disclaimer, the term of this patent is extended or adjusted under 35 U.S.C. 154(b) by 253 days.

(21) Appl. No.: 17/662,052

(22) Filed: May 4, 2022

(65) Prior Publication Data

US 2022/0370023 A1    Nov. 24, 2022

(30) Foreign Application Priority Data

May 19, 2021    (DE) ............... 10 2021 002 629.2

(51) Int. Cl.
*A61B 6/10*    (2006.01)
*A61B 6/00*    (2024.01)

(52) U.S. Cl.
CPC ............ *A61B 6/105* (2013.01); *A61B 6/4405* (2013.01); *A61B 6/4441* (2013.01)

(58) Field of Classification Search
None
See application file for complete search history.

(56) References Cited

U.S. PATENT DOCUMENTS

2012/0212308 A1*  8/2012  Herrmann ............ A61B 6/4441
                                                               335/219

* cited by examiner

*Primary Examiner* — Edwin C Gunberg
(74) *Attorney, Agent, or Firm* — Knobbe, Martens, Olson & Bear LLP (57) ABSTRACT

A device for implementing a latching function of an adjustment axis of an X-ray C-arm comprises at least two magnetic bodies and two components of the adjustment axis that are movable relative to one another. A first component of the two relatively movable components of the adjustment axis is operatively connected to a magnetic body of the at least two magnetic bodies. A second component of the components of the adjustment axis movable relative to one another is a component of the X-ray C-arm system and the second magnetic of the at least two magnetic bodies is operatively connected to this component.

14 Claims, 8 Drawing Sheets

Figure 4B

DEVICE FOR IMPLEMENTING A LOCKING FUNCTION OF AN ADJUSTMENT AXIS OF AN X-RAY C-ARM SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to the field of medical imaging devices and more specifically to mechanical adjustment of such devices.

Description of the Related Art

During the operation of a medical X-ray C-arm system, appropriate adjustment axes can be set for recording images from different positions, so that an examination region or a region of interest (ROI) can be recorded from different viewing angles. An X-ray C-arm system carries an X-ray generator at one end and an X-ray image detector at the other end and opposite the X-ray generator. Correspondingly, the adjustment axes of the X-ray C-arm can be adjusted three-dimensionally manually or by motor control, it being possible for the adjustment axes to have sensors for detecting the extent of the adjustment.

It is of particular interest in this regard that selected positions and the viewing angles thereof can be retrieved for the user reliably, reproducibly and in a user-friendly manner and readjusted in order to generate images from these viewing angles.

The mechanism in which an adjustment axis is adjusted into an intended position and locks in that position, i.e. is held (fixed), is referred to as a catch.

In conventional systems, adjustment axes are held by means of a mechanical catch, for example, a prestressed ball (e.g., a spring-prestressed ball) is pressed or pressed into a counterpart for fixation purposes; such a counterpart for fixation purposes can be a catch plate, for example.

However, a disadvantage of such a mechanical configuration of the holder of an adjustment axis is that, for a mechanical contact of this kind or a mechanical contact configured in some other way, this type of holder entails mechanical wear. This may mean that a readjustment may be necessary in case of an increased degree of wear, or the mechanical catch must be completely replaced in the case of considerable wear, in order to enable a non-slip (e.g., positionally accurate) fixation of an adjustment axis, which entails a considerable outlay.

SUMMARY

An example problem addressed by certain embodiments of the present technology is that of providing an improved device for implementing a latching function of an adjustment axis. Without limiting the scope of the present disclosure, certain advantageous features are recited in the claims of the present application.

In a first aspect, a device for implementing a latching function of an adjustment axis of an X-ray C-arm comprises at least two magnetic bodies and at least two components of the adjustment axis that are movable relative to one another. A first component of the two relatively movable components of the adjustment axis is operatively connected to a first magnetic body of the at least two magnetic bodies. A second component of the two relatively movable components of the adjustment axis is a component of the X-ray C-arm system. A second magnetic body of the at least two magnetic bodies is operatively connected to the second component.

In some embodiments, the operative connection of at least one of the first and second magnetic bodies to the corresponding component of the adjustment axis is a friction fit, an integral bond, or an interlocking connection.

In some embodiments, each of the at least two magnetic bodies is a diamagnet, a paramagnet, a ferromagnet, or an electromagnet.

In some embodiments, each of the at least two magnetic bodies is operatively connected internally to the corresponding component of the adjustment axis.

In some embodiments, the adjustment axes are fixed at least one of rotationally or translationally.

In some embodiments, the at least two components of the adjusting axis are mounted such that they can be moved under motor power and/or manually.

In some embodiments, the at least two magnetic bodies are electro magnetics, and wherein the latching function can be switched off.

In some embodiments, the device further comprises a spring device configured to generate an acoustic signal during the latching function.

In some embodiments, at least one of the at least two magnetic bodies is operatively connected to one of the at least two components of the adjustment axis that are movable relative to one another.

In some embodiments, the X-ray C-arm system is a mobile X-ray C-arm or a fixedly installed X-ray C-arm.

DETAILED DESCRIPTION

The present disclosure is directed to devices for implementing a latching function of an adjustment axis of an X-ray C-arm. A problem addressed by some embodiments of the present technology is that of providing an improved device for implementing a latching function of an adjustment axis. In some embodiments of the present technology, a device is used for implementing a latching function of an adjustment axis of an X-ray C-arm system. The device can include at least two magnetic bodies and two components of the adjustment axis that are movable relative to one another. A first component of the two components of the adjustment axis that are movable relatively to one another can be operatively connected to one of the at least two magnetic bodies. The second component can be a component of the X-ray C-arm system and the second magnetic body of the at least two magnetic bodies can be operatively connected to this component.

The latching function effected by the device according to the present technology can also be considered, for example, an adjustment, a retention, or a fixation along a corresponding adjustment axis at one or more positions along the adjustment axis. The possible fixable adjustment axes in the case of an X-ray C-arm system can be one, several, or all adjustment axes, for example, the orbital axis and/or the angulation axis and/or the horizontal axis and/or the vertical axis.

The at least two magnetic bodies used according to the present technology can have different types of magnetism. For example, the magnetic bodies can be ferromagnets, paramagnets, diamagnets, ferrimagnets, permanent magnets, or electromagnets. The at least two magnetic bodies used can also have different types of magnetism independently of one another. For example, one of the at least two magnetic bodies can be a ferromagnet, while the other of the at least two magnetic bodies can be a paramagnet. However, all the magnetic bodies used can also have the same type of magnetism. For example, the at least two magnetic bodies used can both be electromagnets.

Furthermore, the device can include two components of the adjustment axis which are movable relative to one another. The first component can be operatively connected to one of the at least two magnetic bodies, which magnetic body can be mounted (e.g., fastened), operatively connected to the inner side or the outer side of the adjustment axis. In some embodiments, the at least two magnetic bodies can be equally distributed in number over the two components of the adjustment axis that are movable relative to each other. If more than two magnetic bodies are present, they can also be distributed in unequal proportions, (e.g., asymmetrically) over the two components of the adjustment axis movable relative to one another. A magnetic body can be composed of a plurality of magnets if more than at least two magnetic bodies are present, for example, by stacking a plurality of magnetic bodies one on top of the other. In this case, the magnetic bodies stacked one on top of the other can be held together, such as by magnetic forces, and a stack of magnetic bodies can be regarded according to the present technology as a magnetic body. When magnets stacked one on top of the other are used, it can be advantageous if the acting magnetic force can be exactly metered, depending on the number of magnets stacked one on top of the other. Furthermore, using magnets stacked one on top of another can be beneficial economically, since only the number of magnets needed to achieve a predetermined magnetic force can be used.

The second component of the two components of the adjustment axis that are movable relatively to one another can be a component of the X-ray C-arm system and the second magnetic body of the at least two magnetic bodies can be operatively connected to this component. The at least two magnetic bodies can be operatively connected in such a manner that no gaps, grooves, lacunae or other openings are present or created in which difficult-to-clean impurities could accumulate. The devices according to the present technology can thus meet the high standards of clinical cleanliness requirements, and usage is beneficially wear-free. In some embodiments, the second component can be the housing of the X-ray C-arm system and may be a traveling stand or a part of the traveling stand, the swivel arm for example, on which the second component can be mounted and connected. The relative movability of the two components of the adjustment axis makes it possible for the first or the second component to be mounted in a connected state, and thus the second or the first component can have mobility, or both components can have mobility and thus assume one or more positions relative to one another.

In some embodiments, the present technology advantageously provides for wear-free operation of the device, since mechanical contacting is no longer necessary due to the use of magnets.

Another advantage of certain embodiments of the present technology is that it can be used in any X-ray C-arm system, e.g., in mobile X-ray C-arm systems as well as in fixedly installed stationary X-ray C-arm systems.

An additional advantage of the present technology can be the avoidance of noise when the locking position has been reached.

A further advantage of the present technology can be the improved haptic properties of the device, for example, due to the magnetic action of the device instead of the use of mechanical latching devices.

Alternative configurations provide that the operative connection of the at least two magnetic bodies to the adjustment axis is accomplished by a friction fit, integral bonding or interlocking. In a frictionally fitting operative connection, the magnetic body and the corresponding component can be clamped together or one into another. In an integrally bonded operative connection, the magnetic body and the corresponding component can be, for example, soldered, welded or adhesively bonded. In an interlocking operative connection, the magnetic body and the component can be connected, for example, by means of a third component such as by riveting or a threaded connection. According to the present technology, said components can be operatively connected by means of further guiding and fixing devices.

Various embodiments of the present technology provide that the magnetic bodies can be permanent magnets, diamagnets, ferrimagnets, ferromagnets, and/or electromagnets.

Various embodiments of the present technology provide that the magnetic bodies can be operatively connected and/or internally mounted on the relative components of the adjustment axis. The operative connection of the at least two magnetic bodies to the movable component of the adjustment axis can be accomplished by a friction fit, integral bonding, or interlocking. In a frictionally fitting operative connection, the magnetic body and the internal part of the adjustment axis can be clamped together or one into another. In an integrally bonded operative connection, the magnetic body and the internal part of the adjustment axis can be, for example, soldered, welded or adhesively bonded. In an interlocking operative connection, the magnetic body and the internal part of the adjustment axis can be connected, for example, by means of a third component, e.g., by welding or screwing the magnetic body to a component of the adjustment axis. This can have the advantage that the magnetic bodies are not visibly mounted on the adjustment axis.

Various embodiments of the present technology provide that the adjustment axes can be adjusted rotationally and/or translationally and can have a latching function at corresponding positions.

Various embodiments of the present technology provide that the latching components of the adjusting axes which are movable relative to one another can be mounted in a manner such that they can be moved by motor and/or manually.

Various embodiments provide that the retaining of the components which can move relative to one another can be disengaged, for example, when electromagnets are used in at least one of the at least two magnetic bodies. It can be advantageous in this embodiment if it is possible to enable the device only in manual operation, for example, or only in motor operation.

Various embodiments provide that when the magnetic latching has been achieved, an acoustic signal can be generated, in particular by means of a spring device additionally present for the magnetic latching, for example by means of a magnetic body which is mounted in a separate spring tensioning device. In addition to the magnetic detent, a mechanical catch can also be integrated into the X-ray C-arm system in some embodiments. Advantageously, in addition to haptic information, in these embodiments the user can also receive acoustic information that a corresponding latching position has been reached.

In some embodiments, at least one of the at least two magnetic bodies is operatively connected movably to one of the two components movable relative to one another, the movability being understood as an adjustability of the position, radially and/or tangentially, of at least one of the at least two magnetic bodies.

The present technology will be described in greater detail below with reference to the figures.

Figure 1:
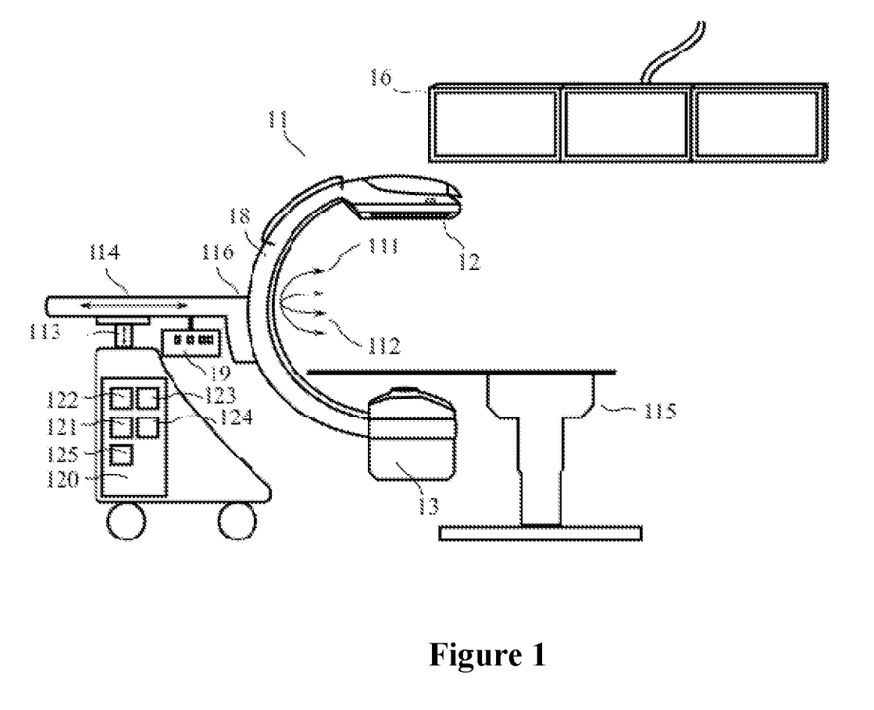
FIG. 1 shows a mobile X-ray C-arm system having multiple adjustment axes.

FIG. 1 schematically shows an X-ray C-arm system 11, which is provided for recording projection images of a 3D scan.

The C-arm 18 carries an X-ray generator 13 at one end and an X-ray image detector 12 at the other end and opposite the X-ray generator 13. The C-arm 18 can be adjusted in a plurality of adjustment axes (111, 112, 113, 114) in space by motor and/or manually, the axes having sensors for detecting the extent of the adjustment. The C-arm 18 can also be adjusted along an orbital adjustment axis 111 (orbital axis). It is also possible to adjust the C-arm 18 along an angulation axis 112. A further adjustment possibility, along the horizontal plane, is provided by the adjustment axis 114 (carriage), which makes it possible to guide the C-arm 18 back and forth. For example, the C-arm 18 can thus be moved closer to or away from an operating table 115 without moving the X-ray C-arm system 11. A further adjustment possibility is offered by the vertical adjustment axis 113, so that the C-arm 18 can be adjusted in height.

The apparatus further includes a computer 120 having a memory unit 121, a reconstruction unit 122, a control unit 123, an image processing unit 124, and a network interface 125.

The projections used for reconstructing a 3D volume can be stored or loaded into the memory unit 121. Said projections can either be loaded from a server or recorded by means of the X-ray C-arm system 11 before or during an intervention. The reconstruction unit 122 reconstructs the 3D volume from the projections present in the memory unit 121. An image processing unit 124 creates a 3D view of the 3D volume with variable 3D views and for defining sectional planes for sectional image representations. Furthermore, the device includes a GUI with an image output unit 16 and an input unit 19, with which the image processing unit 124 and the control unit 123 can change the sectional planes. If the user determines during the analysis of the 3D volume that he needs a further recording from a specific viewing angle, he can reliably and reproducibly adjust this viewing angle by means of the settings of the corresponding adjustment axes (111, 112, 113, 114) and the device according to the present technology.

Figure 2A:
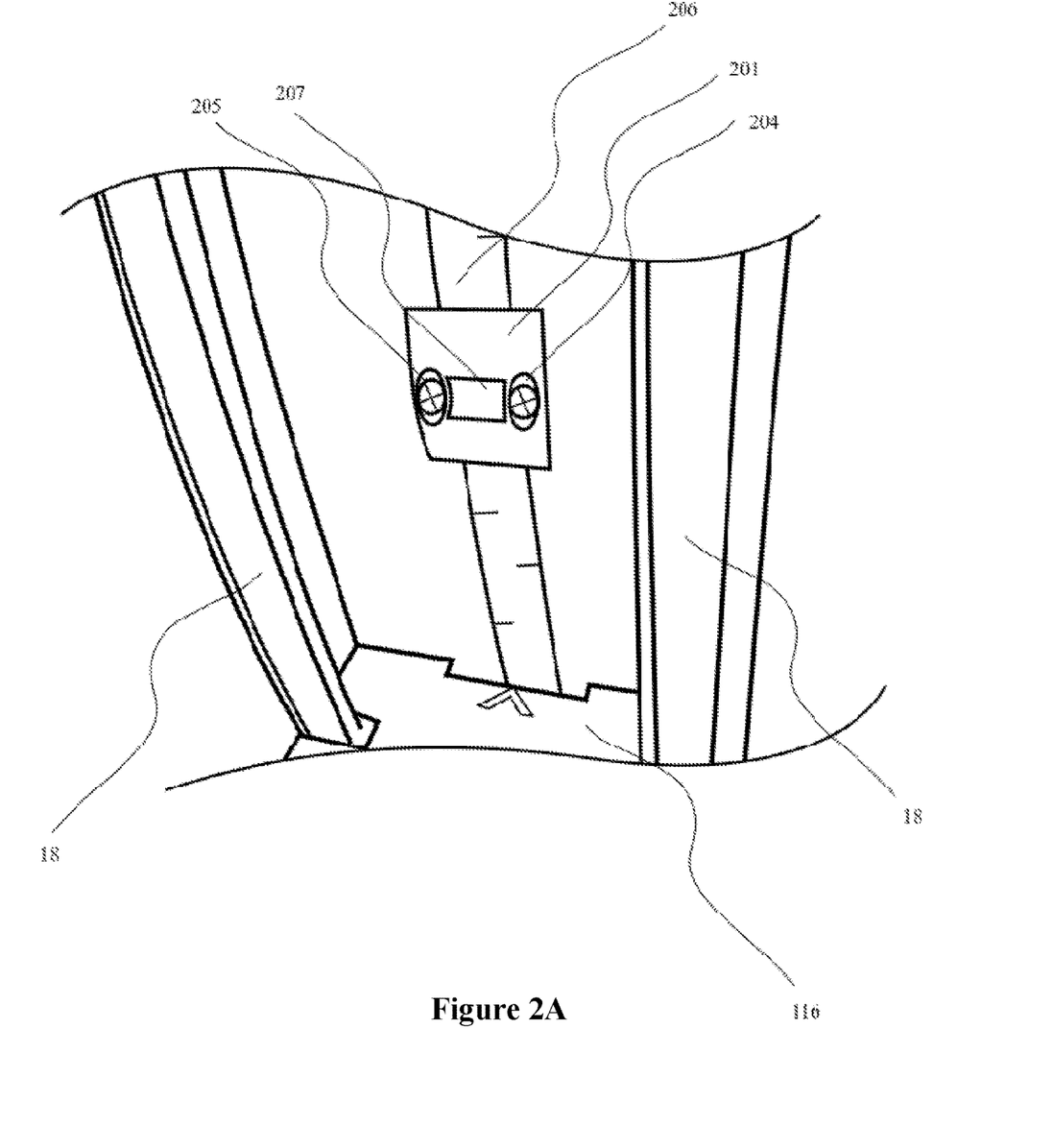
FIGS. 2A, 2B, 2C and 2D show an example mechanical latching device.
Figure 2B:
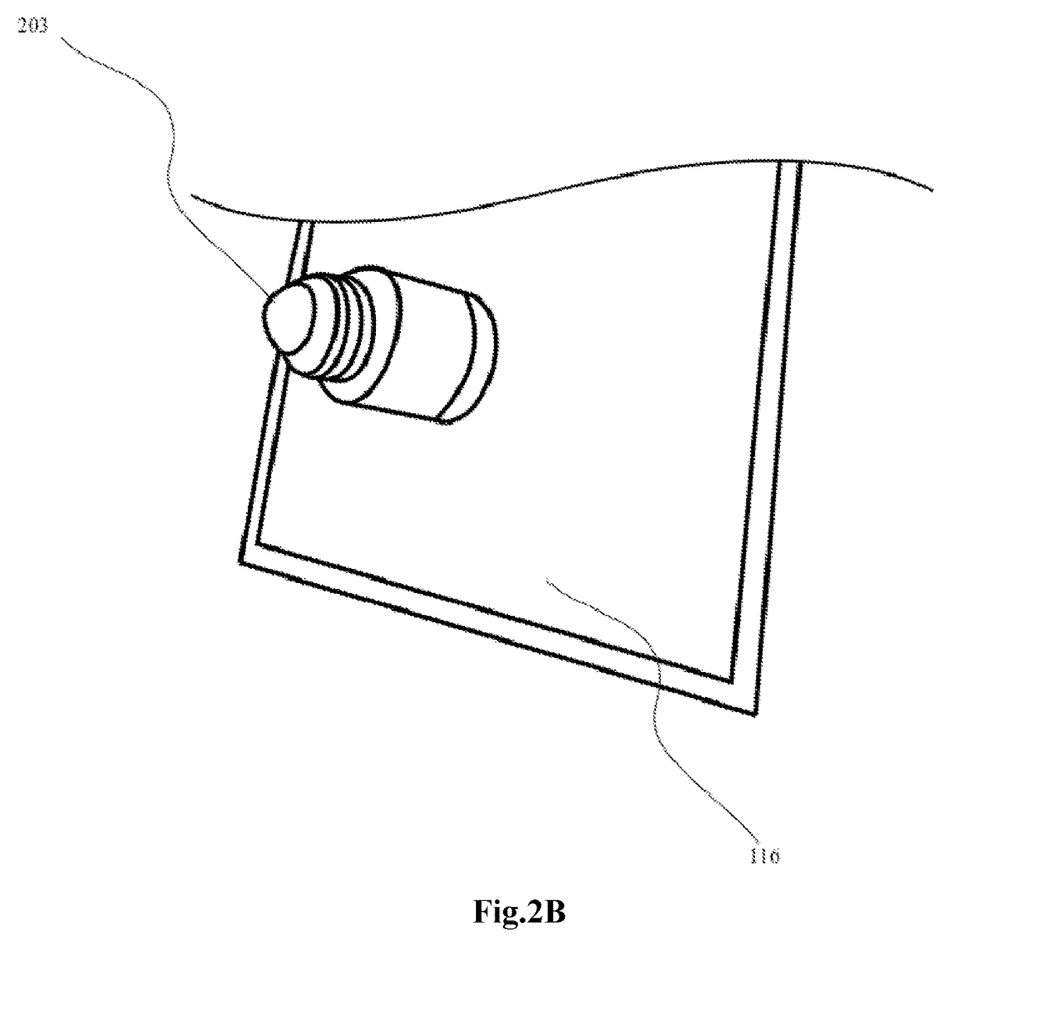

FIGS. 2A and 2B show a mechanical latching device. In this configuration, a C-arm 18 is moved along its orbital axis. There is a scale on the C-arm 18 by means of which it is possible to read the degree by which the C-arm 18 has been moved along the orbital axis. On the C-arm 18 there is additionally a latching plate 201 with a latching surface 207 (pressure piece) into which a latching button 203 can be pressed, preferably by means of a spring tensioning device. The latching button is located in the swivel arm 116 of the C-arm. Furthermore, the latching plate 201 has an adjusting region 204 with which the position of the latching plate 201 can be readjusted, for example due to wear and tear caused by the mechanical stress exerted by the latching button 203 on the latching surface 207. Adjusting screws 205 are available for the readjustment, which, by loosening and fixing, make it possible to adjust the detent plate 201 and thus to reposition the latching surface.

Figure 2C:
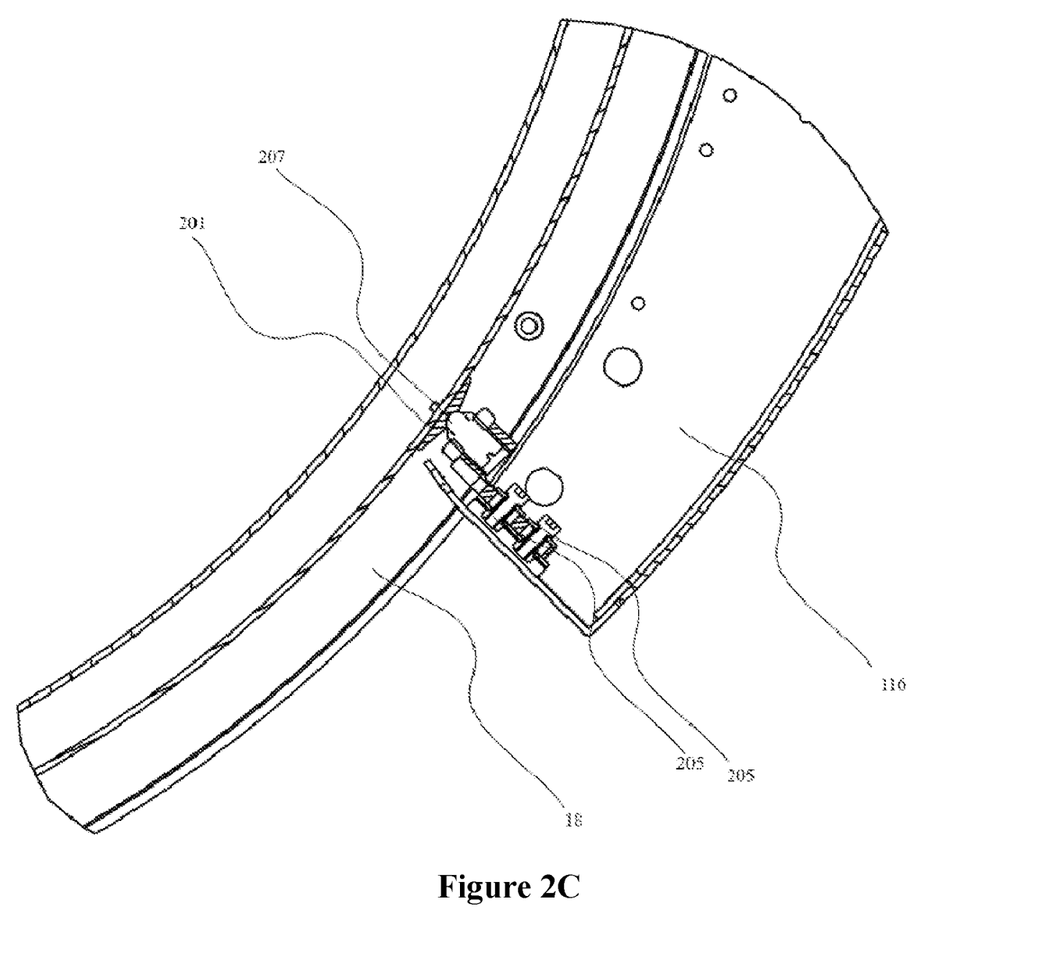
Figure 2D:
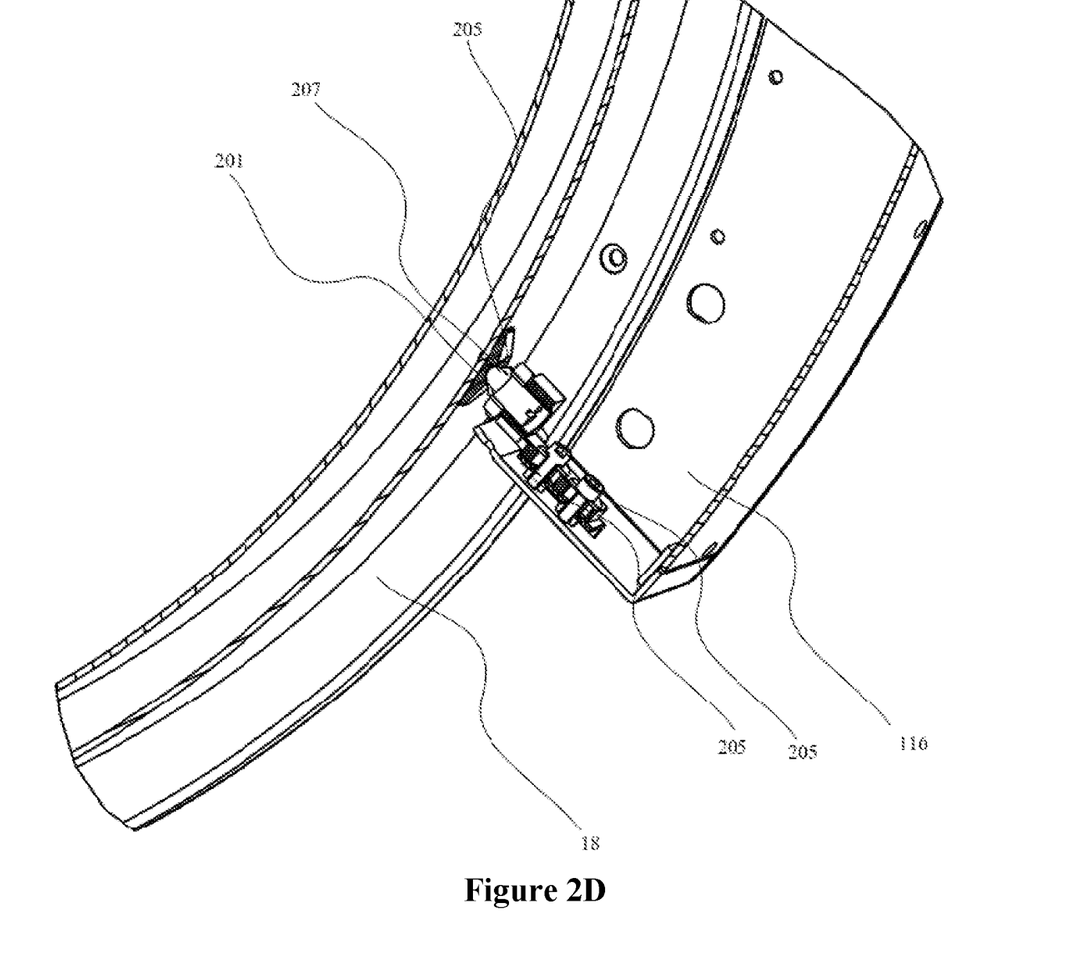

FIGS. 2C and 2D show an alternative embodiment of a mechanical latching device. In this configuration, a C-arm 18 is moved along its orbital axis. There is a scale on the C-arm 18 by means of which it is possible to read the degree by which the C-arm 18 has been moved along the orbital axis. On the C-arm 18 there is additionally a latching plate 201 with a latching surface 207 (pressure piece) into which a latching button 203 can be pressed, preferably by means of a spring tensioning device. The latching button is located in the swivel arm 116 of the X-ray C-arm system. Furthermore, the latching plate 201 has an adjusting region 204 with which the position of the latching plate 201 can be readjusted, for example due to wear and tear caused by the mechanical stress exerted by the latching button 203 on the latching surface 207. Adjusting screws 205 are available for the readjustment which, by loosening and fastening, make it possible to adjust the latching plate 201 and thus to reposition the latching surface.

Figure 3:
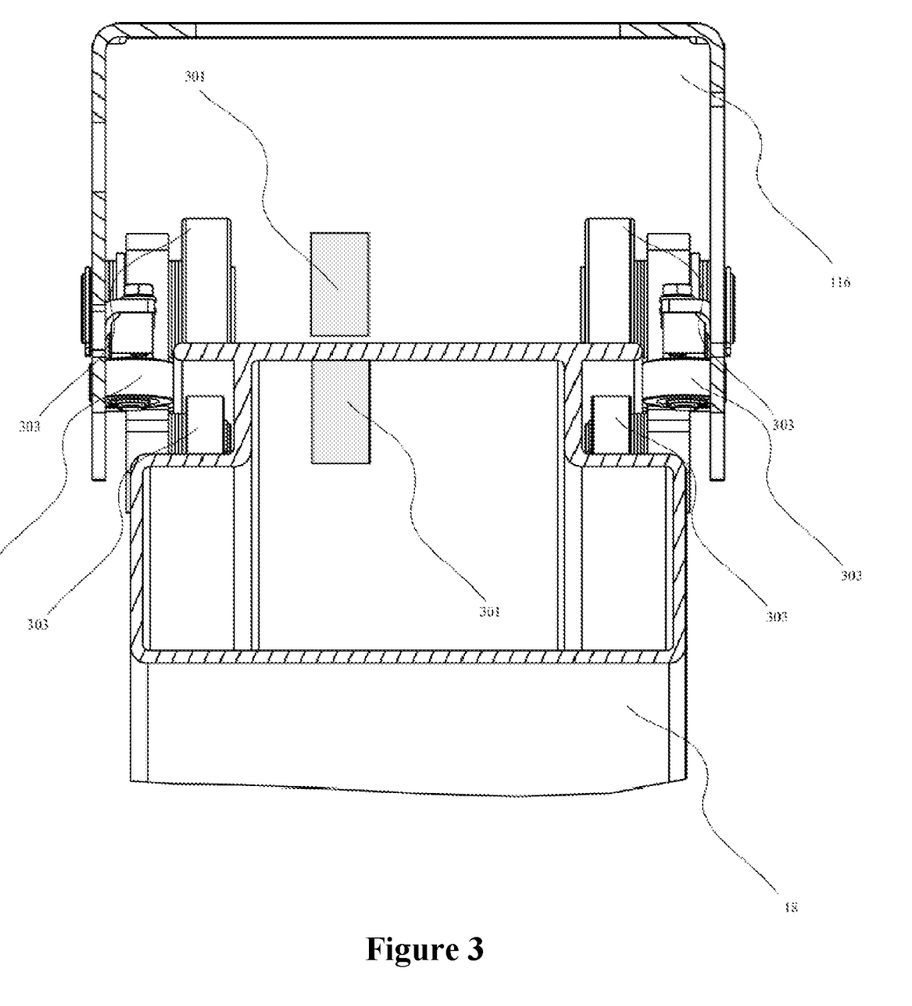
FIG. 3 shows an example arrangement of the magnetic bodies in an adjustment axis.

FIG. 3 shows an embodiment of the present technology in which a magnetic body 301 is accommodated in the swivel arm 116 of an X-ray C-arm system 11. A second magnetic body 301 is accommodated in the C-arm 18. The C-arm 18 can be moved by motor or manually by the rollers 303 mounted in the swivel arm 116 of the C-arm 18. Both magnetic bodies 301 can be ferromagnets, permanent magnets or electromagnets, or the at least two magnetic bodies can have a different type of magnetism. It is also possible if one of the two magnetic bodies is a permanent magnet while the other magnetic body can be an electromagnet (e.g., the two magnetic bodies can have different types of magnetism). If the two magnetic bodies face one another directly, the magnetic force between the two magnetic bodies is maximal, whereby the C-arm latches (e.g., is fixed, adjusted or held in this position). Even after a short movement path in front of or behind the magnetic body 301, the magnetic effect may be too small to enable holding (e.g., fixing or adjustment) of the adjustment axis. If the two magnetic bodies 301 are directly opposite one another, then the maximum magnetic attraction force acts between these two magnetic bodies 301, so that the adjustment axis is fixed. In addition to the magnetic latching, which is accomplished by the magnetic bodies 301, a spring-loaded holding can also be realized as a supplement, as shown in FIGS. 2A, 2B, 2C and FIG. 2D, so that acoustic feedback takes place when a specific latching position is reached.

Figure 4A:
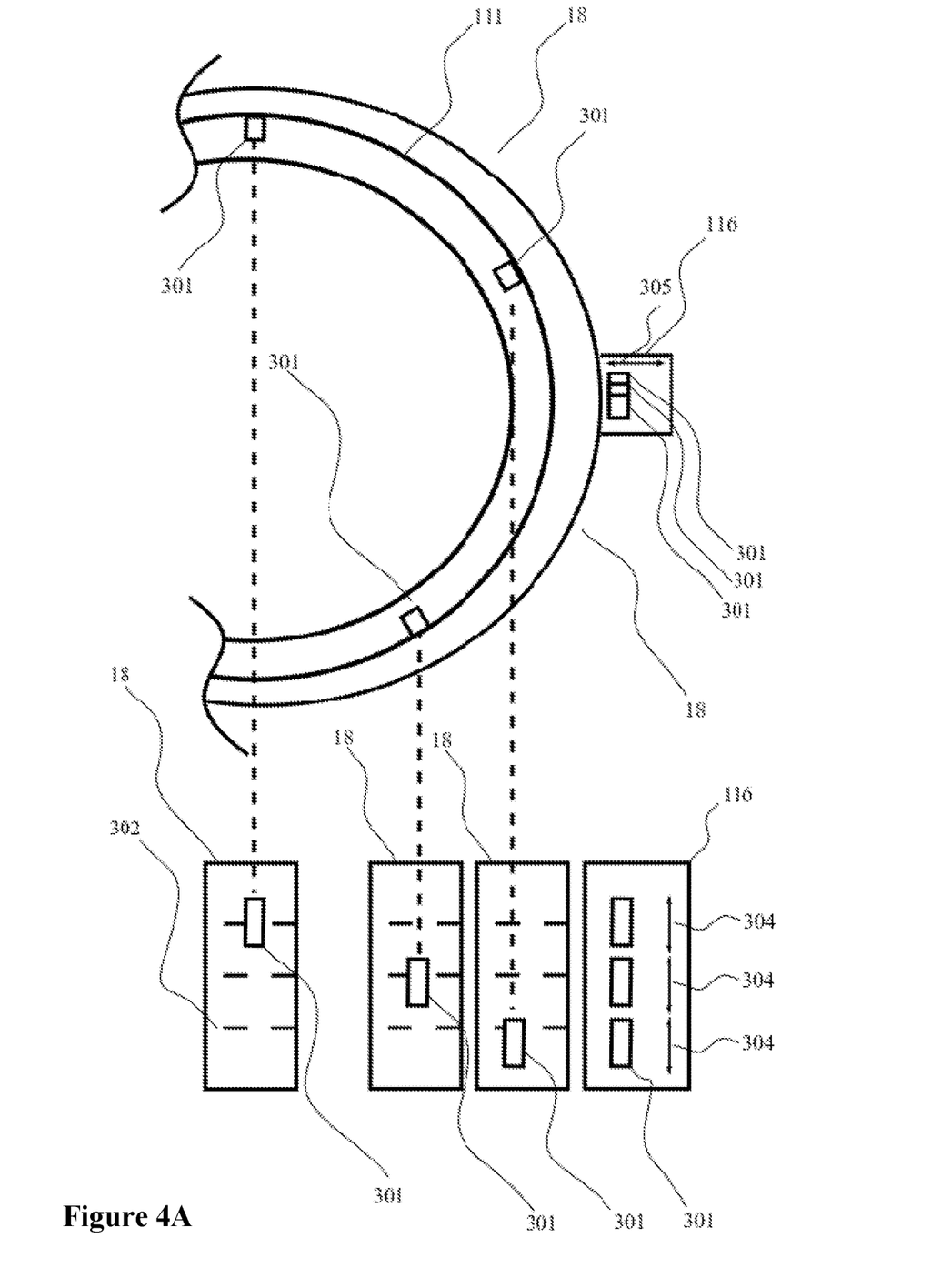
FIGS. 4A and 4B show alternative embodiments of the device according to the present technology, in which a plurality of magnetic bodies are operatively connected movably to one of the two components that are movable relatively to one another.
Figure 4B:
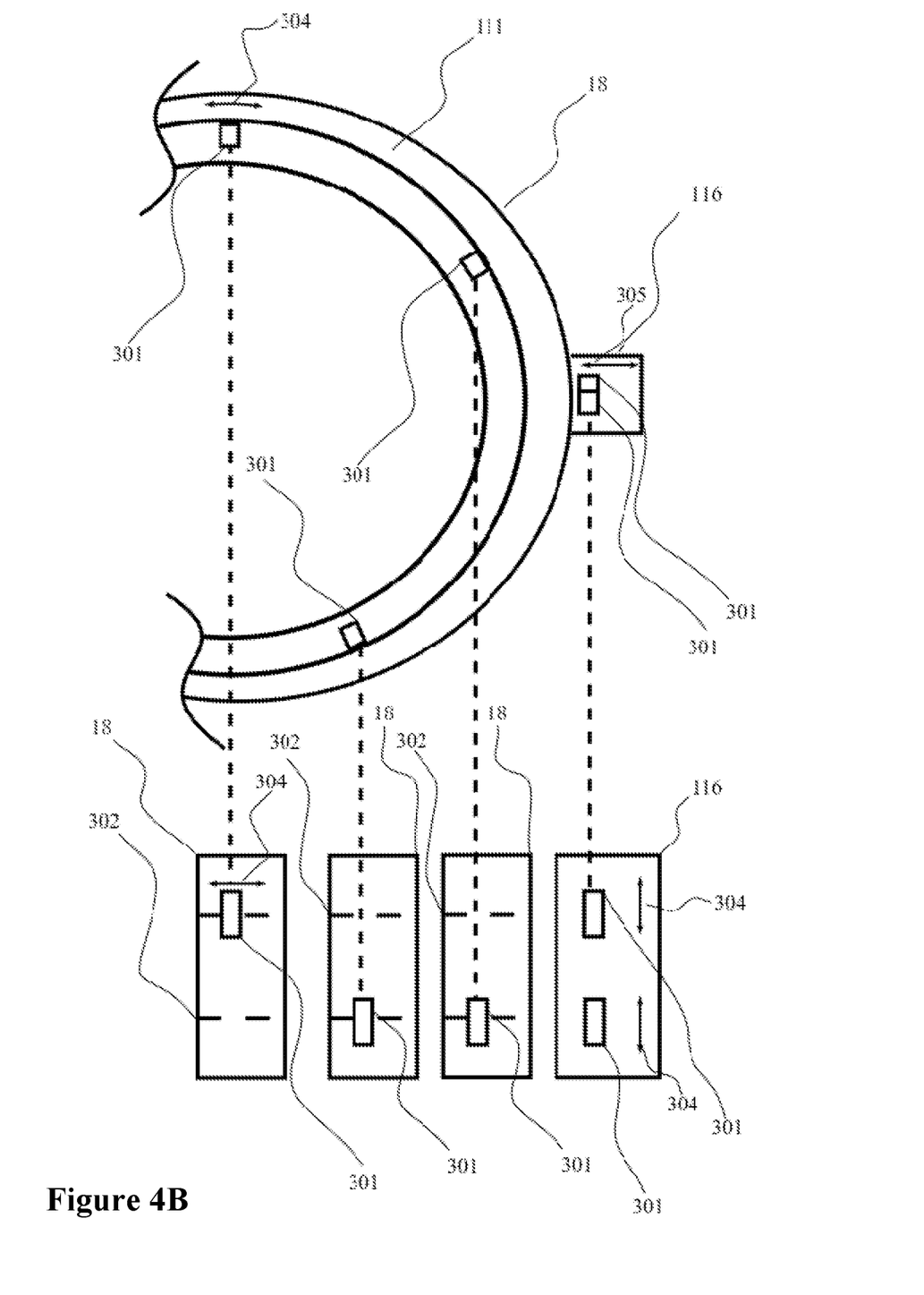

FIGS. 4A and 4B show further developed embodiments of the present technology, in which a plurality of magnetic bodies 301 are operatively connected movably to one of the two components that are movable relatively to one another.

This is illustrated in FIG. 4A with the aid of three magnetic bodies 301 in the swivel arm 116 and three magnetic bodies 301 of the X-ray C-arm system 18 (orbital adjustment axis 111), and is illustrated in FIG. 4B with the aid of two magnetic bodies 301 in the swivel arm 116 and three magnetic bodies 301 in an X-ray C-arm system 18 (orbital adjustment axis 111), two of the three magnetic bodies 301 being located on a path 302 in FIG. 4B.

A plurality of magnetic bodies, which are operatively connected to the movable component of an adjustment axis, make it possible to achieve a latching position at multiple points on the orbital adjustment axis 111; in the case of an orbital adjustment axis 111, this applies in particular to those viewing angles which may be of greater relevance to the user, for example, 45°, 90° or 180°. The magnetic bodies 301 can also be situated on tracks 302. A further magnetic body 301, which is required for implementing the latching device, is located in the swivel arm 116, wherein (e.g., when several paths 302 are present) a correspondingly equal number of magnetic bodies 301 may also be present in the swivel arm 116. The magnetic bodies 301, which are operatively connected to the swivel arm 116, can be mounted so as to be adjustable in multiple directions, for example in the tangential direction 304 and/or in the radial direction 305. For example, tolerances of the X-ray C-arm system, especially manufacturing tolerances, can be compensated by means of these adjustment possibilities. There is also the possibility of regulating the attractive forces of the magnetic bodies 301 by means of the adjustment possibilities, in particular by means of the radial adjustment possibility 305, for example in order to regulate (e.g., to adjust) the strength of the latching function.

In FIG. 4B, furthermore, two magnetic bodies 301 are integrated and operatively connected on a path 302 in the orbital adjustment axis 111, one of the two magnetic bodies being mounted so as to be adjustable tangentially 304, in which case the adjustment (e.g., an individual adjustment of the magnetic body 301) can compensate for manufacturing tolerances of the X-ray C-arm system, in particular for this position. It is likewise possible to adjust the magnetic body 301, which is operatively connected to the orbital adjustment axis 111, in other directions as well. It can be advantageous in such a configuration if, in the case of a non-wide C-arm 18, multiple latching positions can thus be achieved, in particular precisely, especially owing to the adjustability of the magnetic body 301, although the number of paths is limited on account of the width.

LIST OF REFERENCE NUMBERS

11 X-ray C-arm system
12 X-ray image detector
13 X-ray generator
16 Image output unit
18 C-arm
19 Input unit
111 Orbital adjustment axis
112 Angulation adjustment axis
113 Vertical adjustment axis
114 Horizontal adjustment axis (carriage)
115 Operating table
116 Swivel arm
120 Computer
121 Memory unit
122 Reconstruction unit
123 Control unit
124 Image processing unit
125 Network interface
201 Latching plate
202 Housing
203 Latching button
204 Adjustment range
205 Adjusting screw
206 Scale
207 Locking surface/pressure piece
301 Magnetic body
302 Tracks
303 Rollers
304 Tangentially adjustable bearing
305 Radially adjustable bearing

What is claimed is:

1. A device for implementing a latching function of an adjustment axis of an X-ray C-arm, the device comprising:
   at least two magnetic bodies; and
   at least two components of the adjustment axis that are movable relative to one another,
   wherein a first component of the two relatively movable components of the adjustment axis is operatively connected to a first magnetic body of the at least two magnetic bodies,
   wherein a second component of the two relatively movable components of the adjustment axis is a component of the X-ray C-arm system,
   wherein a second magnetic body of the at least two magnetic bodies is operatively connected to the second component,
   wherein the first magnetic body and the second magnetic body are configured to retain the first component relative to the second component in a first latching position when the first magnetic body is aligned in proximity to the second magnetic body.

2. The device of claim 1, wherein the operative connection of at least one of the first and second magnetic bodies to the corresponding component of the adjustment axis is a friction fit, an integral bond, or an interlocking connection.

3. The device of claim 1, wherein each of the at least two magnetic bodies is a diamagnet, a paramagnet, a ferromagnet, or an electromagnet.

4. The device of claim 1, wherein each of the at least two magnetic bodies is operatively connected internally to the corresponding component of the adjustment axis.

5. The device of claim 1, wherein the adjustment axes are fixed at least one of rotationally or translationally.

6. The device of claim 1, wherein the at least two components of the adjusting axis are mounted such that they can be moved under motor power and/or manually.

7. The device of claim 1, wherein the at least two magnetic bodies are electro magnetics, and wherein the latching function can be switched off.

8. The device of claim 1, further comprising a spring device configured to generate an acoustic signal during the latching function.

9. The device of claim 8, wherein the spring device comprises a latching surface coupled to the first component and a complementary latching button coupled to the second component.

10. The device of claim 1, wherein at least one of the at least two magnetic bodies is operatively connected to one of the at least two components of the adjustment axis that are movable relative to one another.

11. The device of claim 1, wherein the X-ray C-arm system is a mobile X-ray C-arm or a fixedly installed X-ray C-arm.

12. The device of claim 1, wherein at least the first magnetic body or the third magnetic body is radially or tangentially adjustable relative to the first component.

13. The device of claim 1, wherein the at least two magnetic bodies further comprise a third magnetic body operatively connected to the first component and spaced from the first magnetic body along the adjustment axis such that the second magnetic body and the third magnetic body are configured to retain the first component relative to the second component in a second latching position when the second magnetic body is aligned in proximity to the third magnetic body.

14. The device of claim 13, wherein the first magnetic body and the third magnetic body are disposed at different lateral offsets within a width of the first component.

* * * * *